United States Patent
Burchman et al.

(10) Patent No.: US 9,943,617 B1
(45) Date of Patent: Apr. 17, 2018

(54) INLINE INTRAVENOUS FLUID STERILIZER

(71) Applicant: Dartmouth-Hitchcock Clinic, Lebanon, NH (US)

(72) Inventors: Corey A. Burchman, Hanover, NH (US); Steven D. Reinitz, Wyckoff, NJ (US); Kathryn E. Boucher Bi, Bow, NH (US); Renee N. Cottle, Kennesaw, GA (US)

(73) Assignee: B.B.R. Medical Innovations, Inc., Hanover, NH (US)

( * ) Notice: Subject to any disclaimer, the term of this patent is extended or adjusted under 35 U.S.C. 154(b) by 686 days.

(21) Appl. No.: 14/300,194

(22) Filed: Jun. 9, 2014

Related U.S. Application Data

(63) Continuation of application No. 12/749,342, filed on Mar. 29, 2010, now Pat. No. 8,747,764.

(60) Provisional application No. 61/164,254, filed on Mar. 27, 2009.

(51) Int. Cl.
  *C02F 1/32* (2006.01)
  *A61L 2/10* (2006.01)

(52) U.S. Cl.
  CPC ..................... *A61L 2/10* (2013.01)

(58) Field of Classification Search
  CPC ....... A61L 2/0011; A61L 2/10; A61M 1/1656; C02F 1/32; C02F 2303/04; C02F 1/722; C02F 2103/026; C02F 2103/04; C02F 2301/024; C02F 1/36; B01D 61/24
  See application file for complete search history.

(56) References Cited

U.S. PATENT DOCUMENTS

| | | | |
|---|---|---|---|
| 5,768,853 A | 6/1998 | Bushnell et al. | |
| 5,900,211 A | 5/1999 | Dunn et al. | |
| 6,461,569 B1 | 10/2002 | Boudreaux | |
| 7,578,933 B1 * | 8/2009 | Selman | A01K 63/04 |
| | | | 119/260 |

(Continued)

OTHER PUBLICATIONS

Edgewroth, et al., "A 25-Year Study of Nosocomial Bacteremia in an Adult Intensive Care Unit", 1999, pp. 1421-1428, vol. 27, No. 8, Publisher: Lippincott Williams & Wilkins, Inc., Published in: US.
Pittet, et al., "Nosocomial Bloodstream Infection in Critically Ill Patients", "Mortality from Bloodstream Infection", May 25, 1994, pp. 1598-1601, vol. 271, No. 20, Publisher: JAMA, Published in: US.

(Continued)

*Primary Examiner* — Walter D. Griffin
*Assistant Examiner* — Cameron J Allen
(74) *Attorney, Agent, or Firm* — Loginov & Associates; William A. Loginov

(57) ABSTRACT

An inline intravenous (IV) fluid sterilization system can be located within directly upstream of the patient's access point, downstream of any breach points, so as to ensure fluid sterility. The chamber space between the walls is accessed by a fluid inlet port and a fluid outlet port between which the fluid flows. The inlet port is connected to a conduit/tubing from the fluid source and the outlet port is interconnected with a conduit/tubing that is free of breach points and interconnects to the patient access point. The inner wall allows for transmission of UV light into the fluid space. The walls define a space therebetween that is relatively small radially, allowing for a sufficient flow rate, but providing a large surface area and small fluid depth for exposure to the UV light. The UV light is provided by an elongated lamp within a cavity of the inner wall.

5 Claims, 13 Drawing Sheets

(56) References Cited

U.S. PATENT DOCUMENTS

| | | |
|---|---|---|
| 2002/0015662 A1 | 2/2002 | Hlavinka |
| 2002/0023865 A1* | 2/2002 | Northcut .............. B01D 29/114 |
| | | 210/192 |
| 2003/0209501 A1 | 11/2003 | Leung |
| 2004/0051056 A1 | 3/2004 | Disabito et al. |
| 2005/0013729 A1 | 1/2005 | Brown-Skrobot et al. |
| 2005/0061743 A1* | 3/2005 | Buttner ................ A61L 2/0011 |
| | | 210/646 |
| 2006/0157426 A1 | 7/2006 | Petrie |
| 2008/0061005 A1 | 3/2008 | Hopaluk et al. |
| 2008/0210608 A1 | 9/2008 | Abe et al. |
| 2009/0012459 A1* | 1/2009 | Sobue ...................... A61L 2/10 |
| | | 604/29 |
| 2009/0084734 A1 | 4/2009 | Yencho |
| 2009/0230321 A1 | 9/2009 | Chen |

OTHER PUBLICATIONS

Laupland, et al., "Population-Based Assessment of Intensive Care Unit-Acquired Bloodstream Infections in Adults: Incidence, Risk Factors, and Associated Mortality Rate", "Crit Care Med", 2002, pp. 2462-2467, vol. 30, No. 11, Publisher: Lippincott Williams & Wilkins, Published in: US.

Loftus, et al., "Transmission of Pathogenic Bacterial Organisms in the Anesthesia Work Area", "Anesthesiology", 2008, pp. 399-407, vol. 109, Publisher: The American Socieity of Anesthesiologists, Published in: US.

Chang, et al., "UV Inactiviation of Pathogenic and Indicator Microorganisms", "Applied and Environmental Microbiology", Jun. 1985, pp. 1361-1365, vol. 49, No. 6, Publisher: American Society for Microbiology, Published in: US.

* cited by examiner

INLINE INTRAVENOUS FLUID STERILIZER

RELATED APPLICATIONS

This application is a continuation of co-pending U.S. patent application Ser. No. 12/749,342, filed Mar. 29, 2010, entitled INLINE INTRAVENOUS FLUID STERILIZER, which claims the benefit of U.S. Provisional Application Ser. No. 61/164,254, filed Mar. 27, 2009, entitled INLINE INTRAVENOUS FLUID STERILIZER, the entire disclosure of each of which applications is herein incorporated by reference.

FIELD OF THE INVENTION

This invention relates to fluid sterilization systems for use in conjunction with an intravenous (IV) fluid-delivery system and more particularly to sterilization systems employing ultraviolet (UV) radiation.

BACKGROUND OF THE INVENTION

The prevalence of nosocomial (hospital-acquired) infection adversely affects the quality and cost of healthcare globally. Primary bloodstream infections, which are typically precipitated by intravenous infusions, account for 8% of all nosocomial infections. A heightened awareness of transmission of potentially pathogenic bacterial organisms has lead to implementation of various preventative measures. In the United States alone, 50,000 to 120,000 patients per year develop infusion-related bacterial infections. With an average cost of treatment of such infections at $15,000 per incident, the overall cost to this country can exceed 2 billion dollars annually. By way of further background, see Tarara, D. and Wenzel, R. P., *Nosocomial Bloodstream Infection in Critically Ill Patients*, JAMA 1994; 271, 1598-1601; Edgeworth, J., Treacher, D. and Eykyn, S., *A 25-year Study of Nosocomial Bacteremia in an Intensive Care Unit*, Crit. Care Med. 1999; 27:1421-1428; and Laupland, K. B., Zygun, D. A., Davies, D., et al., *Population-based Assessment of Intensive Care Unit-acquired Bloodstream Infection in Adults: Incidence, Risk Factors, and Associated Mortality Rate*, Crit. Care Med., 2002; 30:2462-2467.

In the course of normal medical practice, both the intravenous (IV) fluid (commonly comprising colloid or crystalloid solutions), as well as the internal surfaces of the fluid path (commonly transparent polyvinylchloride (PVC) IV tubing) are sterile. This is to ensure that the parenteral compartment of the patient is not seeded with microbial agents.

Any manipulation or perturbation to the integrity of the closed intravenous system can create an opportunity for a breach in the sterility. One recent, well-controlled study found a mean bacterial colonization rate of fluids of approximately 16%. See, by way of background, Loftus, R W, et al., *Transmission of Pathogenic Bacterial Organisms in the Anesthesia Work Area*, Anesthesiology 109 (2008): 399-407.)

In immuno-compromised patients, and in fluids that may in fact support bacterial growth, the risk for significant infection is ever greater. One such manipulation of the sterile fluid system involves the very common practice of the administration of medications, either by bolus or infusion. This creates the opportunity for contamination of the system at, for example, the fluid interface (e.g. a luer fitting).

A recent study at Dartmouth-Hitchcock Medical Center in Lebanon, N.H., USA found that the lumen of intra-operative stopcock sets and associated fluid interfaces (i.e. luer fittings, etc.), previously found at the onset of surgery to be sterile, yielded positive cultures of bacterial organisms in 32% of the cases investigated, at the conclusion of the operative procedure. Twenty-five percent of patients who had positive stopcocks developed nosocomial infections, twice that of the group that did not have stopcock contamination.

A system that can reliably render the parenteral fluids sterile, once the sterile integrity of the system has been breached, at a point downstream from the provider's last contact with the fluid path would be advantageous. It could thereby limit the exposure of risk to the patient significantly. This can effectively have the potential to save billions of health care dollars and millions of lives.

Presently, there are no available reliable commercial mechanisms for rendering parenteral fluid, or any fluid meant for infusion into patients, re-sterilized in real-time, if the sterile condition is breached, short of replacing the fluid and intravenous tubing assembly.

One possible approach to reducing the risk of re-introducing microbial organisms once the sterile barrier had been breached is to employ an inline microbial filter. A pore size of 0.22 microns is necessary for sterile filtration, but such a smaller pore size rating would typically create a greater resistance to flow, and is not tenable for the general range of IV fluid flow rates required in surgery and in treating critically ill patients. By way of example, necessary ranges for the flow of IV fluid range from 5-1000 ml/hr. Furthermore, periodic removal of such an inline filter as it becomes filled with particulates, and its efficiency diminishes, can leave open the possibility for further breaches in the sterile barrier. Because parenteral fluid line contamination is primarily caused by healthcare provider fluid interface or injection points, aka "breach points," it is necessary to ensure there are no further breach points between the device inlet and the patient's parenteral access point (typically an IV catheter).

Other physicochemical techniques also exist that ensure the sterility of fluids includes the physical methods of heat and/or radiation. These are not necessarily viable options as there may be detrimental effects upon structural components of blood and pharmaceutical products.

Accordingly, it is desirable to provide a system for sterilizing IV fluid downstream of any breach points. The system should desirably perform sterilization efficiently at needed flow rates, can sterilize a wide range of fluids without damaging or chemically degrading them, and that generally operates free of a need for replacement or service during a typical IV treatment cycle.

SUMMARY OF THE INVENTION

This invention overcomes the disadvantages of the prior art by providing an inline intravenous (IV) fluid sterilization system that can be located within the fluid system directly upstream of the patient's access point and downstream of any breach points so as to ensure that fluid entering the patient is sterile. This system avoids the use of filters and other elements that require periodic service by providing a cassette with a pair of concentric inner and outer walls defining a fluid space therebetween that enables capillary flow therethrough. The chamber space between the walls is accessed by a fluid inlet port and a fluid outlet port between which the fluid flows. The inlet port is connected to a conduit/tubing from the fluid source and the outlet port is interconnected with a conduit/tubing that is free of breach points and interconnects to the patient access point. The inner wall allows for transmission of UV light into the fluid space so as to deliver a sterilizing energy to the fluid that is sufficient to kill most or all of any microbiological life therein. The walls define a space therebetween (see wall spacing SW in FIG. 11A) that is relatively small/thin radially (a few millimeters at most), thereby allowing for a sufficient flow rate, but providing a large surface area and small fluid depth for exposure to the UV light. Illustratively, the UV light is provided by one or more elongated lamp(s) that is/are nested within a cavity of the inner wall. The elongated lamp(s) is/are mounted in a base unit that includes a shielding outer canister which includes a UV-opaque material that prevents transmission of UV light to the outside environment. The base unit can further include a clamp for mounting to an IV stand or pole, or other supporting structure. In an embodiment, flow through the fluid chamber occurs from a bottom-located inlet to a top located outlet with respect to the direction of gravity this assists in de-airing the unit and preventing formation of bubbles during use.

In an illustrative embodiment, the cassette is removably mounted within the canister by a plurality of projections in the cassette bottom base cap that interengage axial grooves in the inner wall of the canister. By removably mounting the base cap it can be made readily replaceable/disposable, while allowing the base unit to remain in place and reused. The grooves terminate at perpendicular/orthogonal circumferential slots that allow the cassette to be rotatably locked within the canister against axial pullout when the cassette is fully shrouded by the canister. The cassette can also include a top cap that engages the open rim of the canister when fully shrouded thereby. The top cap includes a pair of fluid connections that can be fixed fittings (such as threaded male/female Luer Lock fittings) secured to the top cap surface, or can be fittings mounted on the ends of tubing sections. In an embodiment, the fluid outlet (directed distally to the patient) includes a tubing mounted against a small-diameter hole that passes through the top cap, and into the fluid space between the inner and outer walls. The inlet (from the source of fluid and one or more proximal breach points) is illustratively located at the opposing, base cap of the cassette, and can include a bridge tubing that is fixed to a small-diameter hole through the base cap that interconnected with the fluid chamber between the walls. The bridge tubing is routed through another, larger-diameter port in the base cap radially outward of the outer wall. Sufficient space remains between the outer side if of the base cap and the confronting surface of the base unit to accommodate the 180-degree curved loop section of the bridge tubing that extends from the inlet and upwardly back through the base cap. The inlet bridge tube passes from the base cap port upwardly along the outer wall, and within the inner volume of the canister to a port passing through the top cap. The inlet bridge tubing terminates in a fitting adjacent to (and external of) the top cap. In this manner, the user can connect the source and the delivery access point tubings at locations adjacent to the exposed top of the cassette.

In an embodiment, the space between the inner and the outer fluid chamber walls can include baffles that assist in guiding fluid along a path between the inlet and the outlet to ensure that all fluid receives a predetermined interval exposure to the sterilizing UV light. The baffles can define a spiral, ramp, or other appropriate fluid-guiding pathway.

BRIEF DESCRIPTION OF THE DRAWINGS

The invention description below refers to the accompanying drawings, of which.

DETAILED DESCRIPTION

Figure 1:
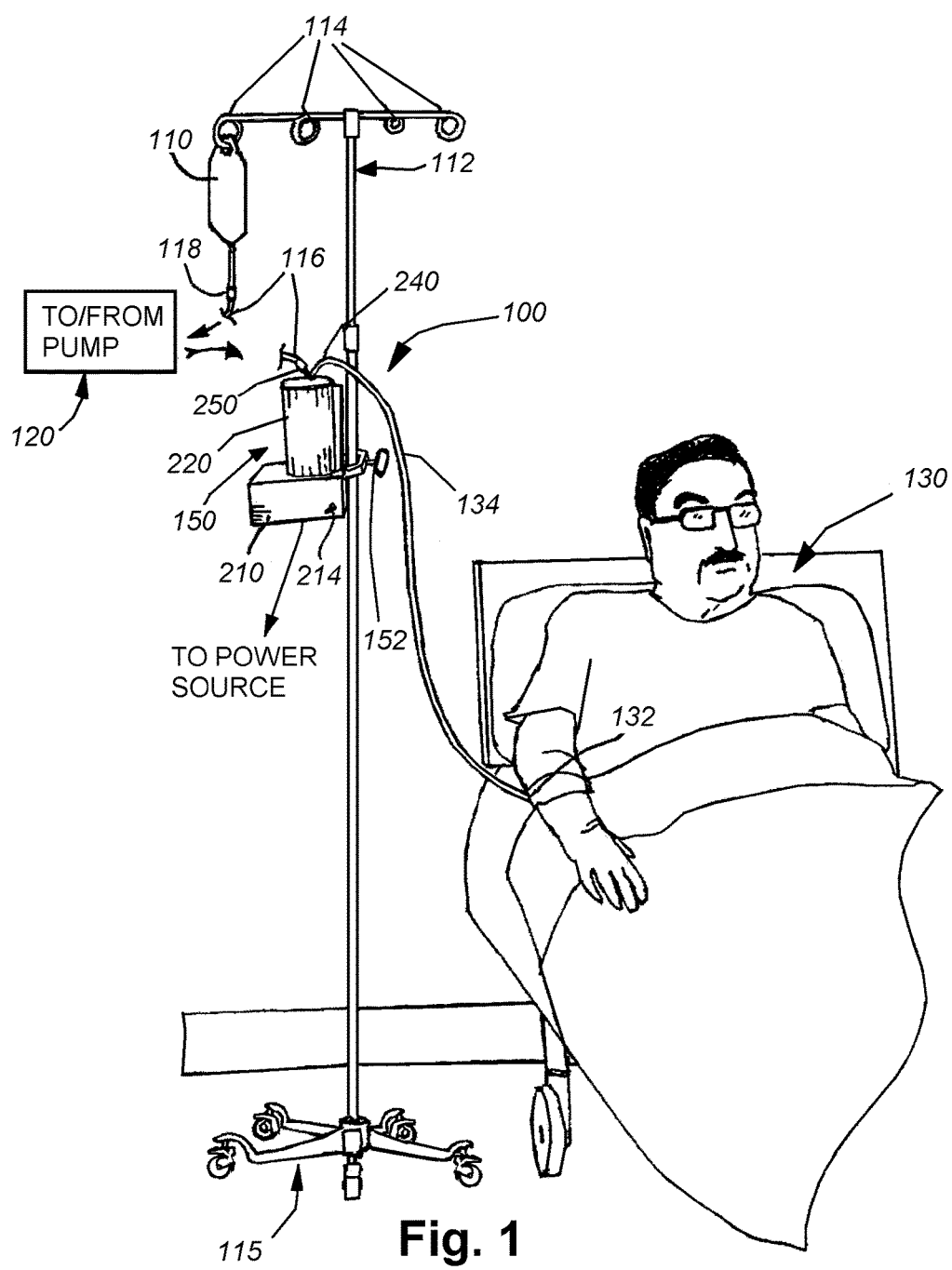
FIG. 1 is an illustration of the inline IV fluid sterilization system shown in use, in conjunction with an IV fluid source and a patient receiving IV fluid delivery through a catheter that acts as an access point therefor.

As shown in FIG. 1, an exemplary arrangement of an intravenous (IV) fluid delivery system 100. The system 100 typically includes a source, such as a conventional IV fluid bag 110, containing an appropriate therapeutic agent in fluid solution. In further embodiments, a combination of fluids, with appropriate mixers and/or stopcock systems can be provided. The bag is mounted on an IV stand or pole 112 including a plurality of associated hanging hooks 114 that are adapted to suspend bags for effective gravity feed of the fluid through a tubing system. The stand can be fixed or portable, as provided by the caster base 115. The bag 110 is adapted to be replaced with a new full bag as needed by manipulating a conventional Luer Lock interconnection 118 and/or a spike interconnection that engages the bag 110. A proximal tubing section 116 is interconnected to the bag via the fitting 118. While not shown, a variety of other fittings can be employed along the tubing 116, including stopcock assemblies that allow for introduction of medicaments via a syringe or other fluid-introduction device. A fluid pump or metering system (120, not depicted) can also be provided inline with the tubing 116 to direct fluid through the system at a predetermined flow rate.

Each of the removably attached fittings along the tubing 116 provides a possible breach point that can allow microbiological contamination to enter the system 100 and its associated fluid flow. This contamination poses a risk of introduction to the patient 130, shown in FIG. 1 receiving IV fluid via a catheter 132 and interconnected tubing 134.

To prevent such potential contamination, the system also includes an inline sterilization system, 150 according to an illustrative embodiment located between the proximal tubing assembly 116 and the distal tubing section and catheter 132, 134. The sterilization system (also termed "sterilizer") 150 is mounted at a convenient location along the IV pole 112 using a conventional clamp 152. It receives power from a standard wall-current source (or batteries, etc.). The power operates an internal UV lamp described in detail below. The UV light emitted from the lamp is employed to sterilize the fluid, and ensure that any contamination occurring at breach points above the sterilizer 150 does not pass into the distally located (with respect to the sterilizer 150) tubing section 134, which is located downstream of likely breach points. In this manner the IV flow to the patient 130 is substantially more likely to remain sterile, and the risk of a nosocomial infection is substantially reduced.

By way of further background, the illustrative embodiment effectively employs ultraviolet (UV) radiation to effectively kill microbiological organisms in a continuous flow of fluid. Successful ultraviolet disinfection has been accomplished in the food service and pharmaceutical industries, as well as water and air purification. UV radiation has been demonstrated to inactivate bacterial and viral microorganisms to a sterility assurance level of up to $10^{-8}$. UV radiation inactivates microorganisms by increasing the energy level of thymine, one of the nucleotides of DNA. This results in DNA destabilization, and programmed cell death ensues within milliseconds.

The illustrative embodiment utilizes the germicidal properties of ultraviolet radiation to render intravenous fluid sterile, particularly where the possibility exists whereby a breach in sterility along a portion of the fluid conduit system has occurred.

Figure 2:
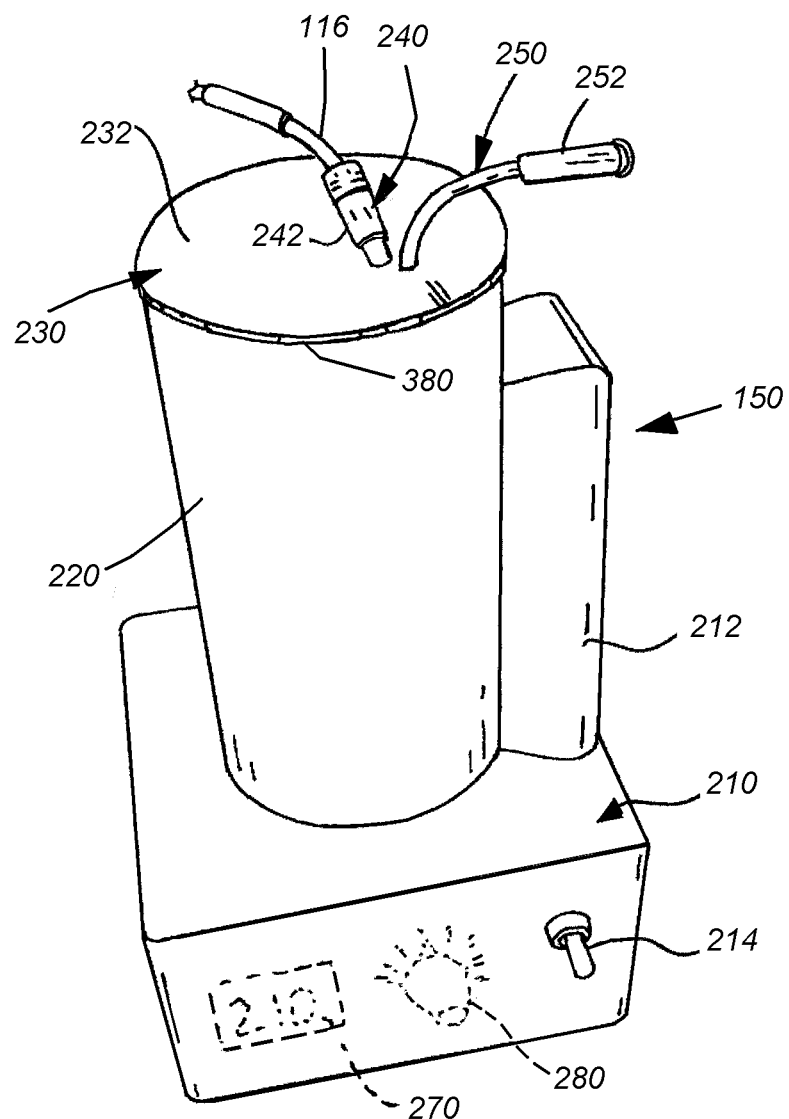
FIG. 2 is a perspective view of the assembled sterilization unit with base unit, the attached canister and cassette inserted thereinto.

With reference to FIG. 2, the sterilization system, or sterilizer 150, is shown in further detail. The sterilizer 150 includes a base unit 210, defining a boxlike enclosure that contains the electronic and electrical elements of the system and more generally provides a supporting structure for the sterilizer's physical components. The internal UV lamp described below is operated by a switch 214. Additional displays and controls can be provided in a manner clear to those of ordinary skill. For example, and as shown in phantom in FIGS. 2 and 3, an alphanumeric output display 270 and/or a variable power switch (e.g. a rheostat) 280 can be provided in an alternate embodiment. Such additional features can provide variable light output to the sterilizer to vary its sterilization effect (i.e. light output) based upon, for example, flow rate. The flow rate can be used as an input parameter that is translated by the system's circuitry into a power output in an embodiment. Illustratively, the sterilizer can include multiple UV-light sources (lamps). The circuitry can be adapted to manually or automatically trigger a second (or more) light source (e.g. a second, parallel elongated lamp) to boost light emission where the flow rate exceeds a predetermined level. This can help to ensure that the fluid receives the needed energy-per-unit-time to appropriately disinfect it. In an alternate embodiment, light can be provided by a solid state source, such as an UV-emitting LED array or a fiber, optic array. The emission of an appropriate amount of UV light can be controlled, at least in part, by activating and deactivating, and/or modulating, various discrete elements of the array.

A clamp support 212 extends upwardly from the top surface of the enclosure of the base unit 210. The clamp support 212 carries the above-described pole-engaging C-clamp, or another device that allows it to be attached to the IV pole 112. Note that alternate mounting arrangements can be provided when the sterilizer is to be mounted with respect to, for example, an IV pump, cart or other structure. Note also that as used herein, terms as "up," "upward," "outward," "down," "downward," "top," "bottom," "radial," "axial," "distal," "proximal," and the like, are conventions only, and should not be taken as absolute indicators of direction or orientation.

A removable canister 220, which in this embodiment defines a hollow cylinder, extends upwardly from the base unit 210 enclosure surface. As described below, the canister is constructed from a UV-opaque material such as polycarbonate, which can include a UV-resistive filler or coating thereon. The canister 220 encases a removable sterilization cassette 230 having an exposed top cap 232 that engages a top rim 380 of the canister 220. The top cap 232 is shown with a fluid outlet 240 and a fluid inlet 250 projecting externally therefrom. The inlet 250 includes a fitting 242 (for example, a threaded Luer Lock fitting) that allows it to be connected to the source to the system via a source tubing 116. Likewise, the inlet 250 includes an inlet fitting at 252 that can also comprise a Luer Lock. The outlet 240 is connected to the distal tubing 134, which terminates at the patient. The outlet and inlet fittings 242 and 252, respectively, can be male or female as appropriate. Alternate types of fittings can be provided and/or a full-length tubing can be provided to either the inlet or outlet so as to extend completely to the source and/or patient. In an embodiment, one male and one female fitting are provided to conform to various conventional fluid-delivery arrangements. Collectively, the base unit 210 and canister 220 comprise a fixed/reusable lamp or bulb housing (BH), while the sterilizing fluid cassette (SFC) comprises a removable (for service and cleaning or disposable component of the system.

Figure 3:
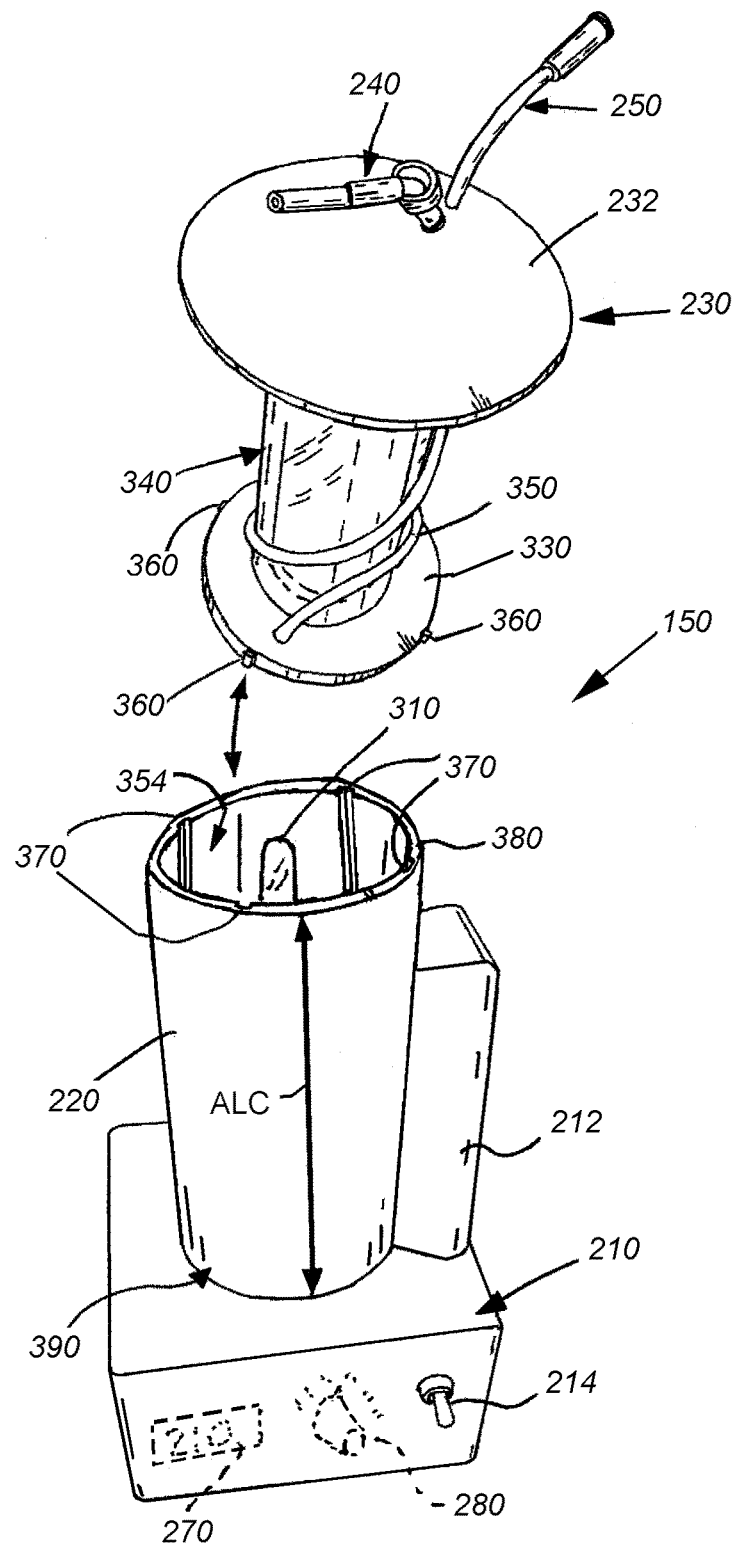
FIG. 3 is an exploded perspective view of the base unit and canister of FIG. 2 with cassette removed, and showing the insertion pathway for the cassette bottom/base cap with respect to the inner surface of the canister.

With further reference to FIG. 3, the cassette 230 is shown removed from the canister 220 and underlying base unit 210. By removing the cassette 230, the central UV light-emitting lamp 310 is revealed. As described below, the cassette 230 includes an opposing bottom cap 330 having a central orifice (1020 below) that allows it to pass over the lamp 310 during insertion and removal. A double-wall fluid chamber assembly 340 extends between the bottom cap 330 and top cap 232. Fluid enters the inlet 250 and passes through the top cap 232, and thereafter through a bridge tube section 350 that runs downwardly outside of the fluid chamber assembly. The bridge tube 350 passes through the bottom cap 330 and loops into a small-diameter inlet located at the bottom side of the bottom cap 330. The fluid is thereafter directed into the space between the double walls (as described further below). Thus, the fluid chamber fills from the bottom up (assisting, along with the capillary action of the thin walls, in de-airing the device and ensuring that bubbles are not retained. Fluid eventually exits through the top cap 232 into the attached outlet tubing 240.

Figure 4:
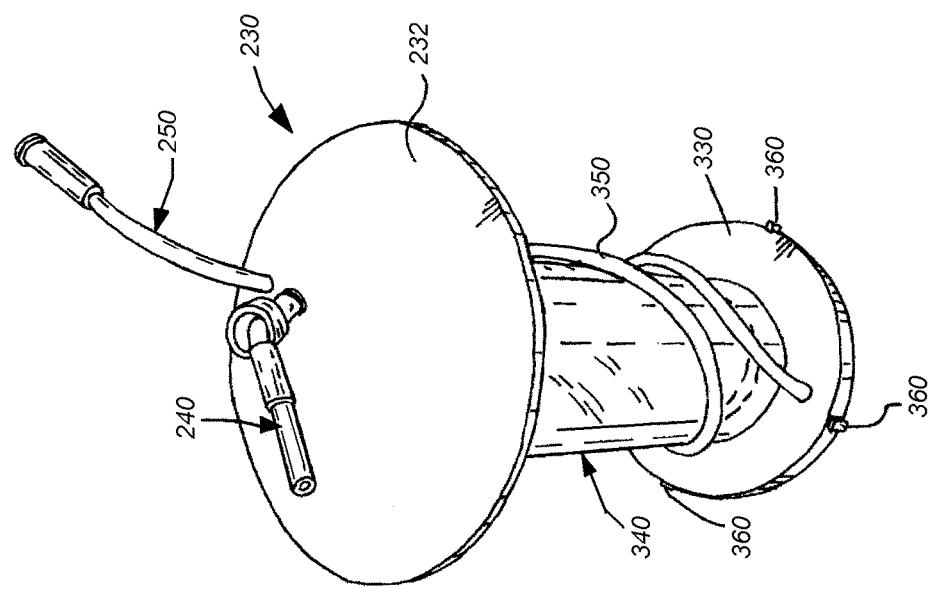
FIG. 4 is a perspective view of the cassette of FIG. 2.

The axial length ALC of the canister 220 is highly variable. In an embodiment, the length ALC is approximately 12 centimeters. However, the length can be varied to accommodate the corresponding length of the lamp 310 as will be described below. The bottom cap 330 is sized to fit flushly against the inner surface 354 of the canister when the cassette 230 is assembled therewith. With further reference to FIG. 4, a set of four lugs 360 extend beyond the outer perimeter of the bottom cap. These lugs 360 are located at 90-degree intervals about the perimeter in an illustrative embodiment. The number of lugs is highly variable, or another locking mechanism structure can be employed. The lugs 360 are sized and arranged to be received by axial grooves 370 formed along the inner surface 354 of the canister 220.

Figure 5:
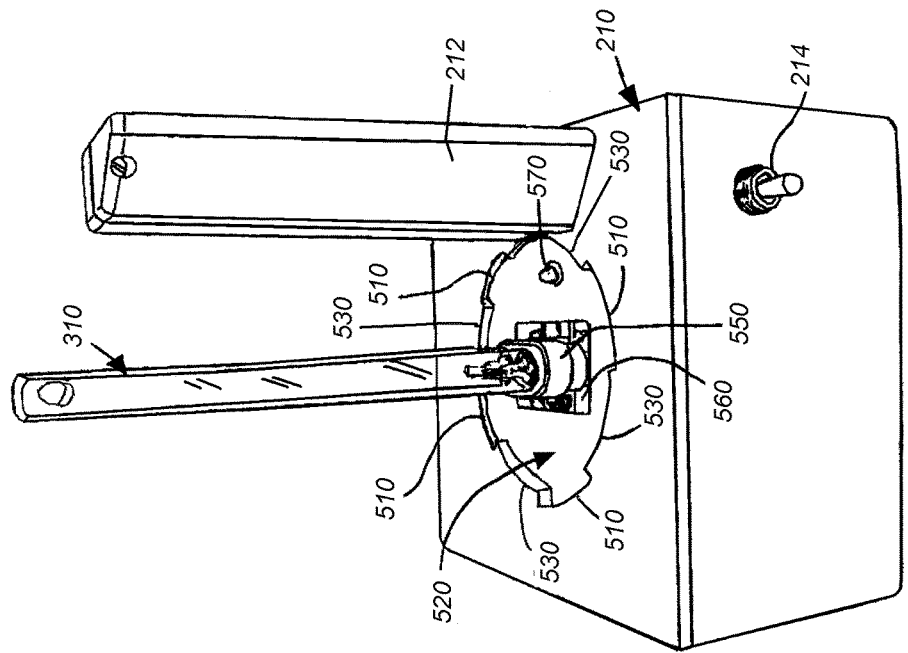
FIG. 5 is a perspective view of the base unit of FIG. 2 with the canister removed therefrom and exposing the elongated UV-emitting lamp and lamp base/socket assembly.
Figures 6, 7:
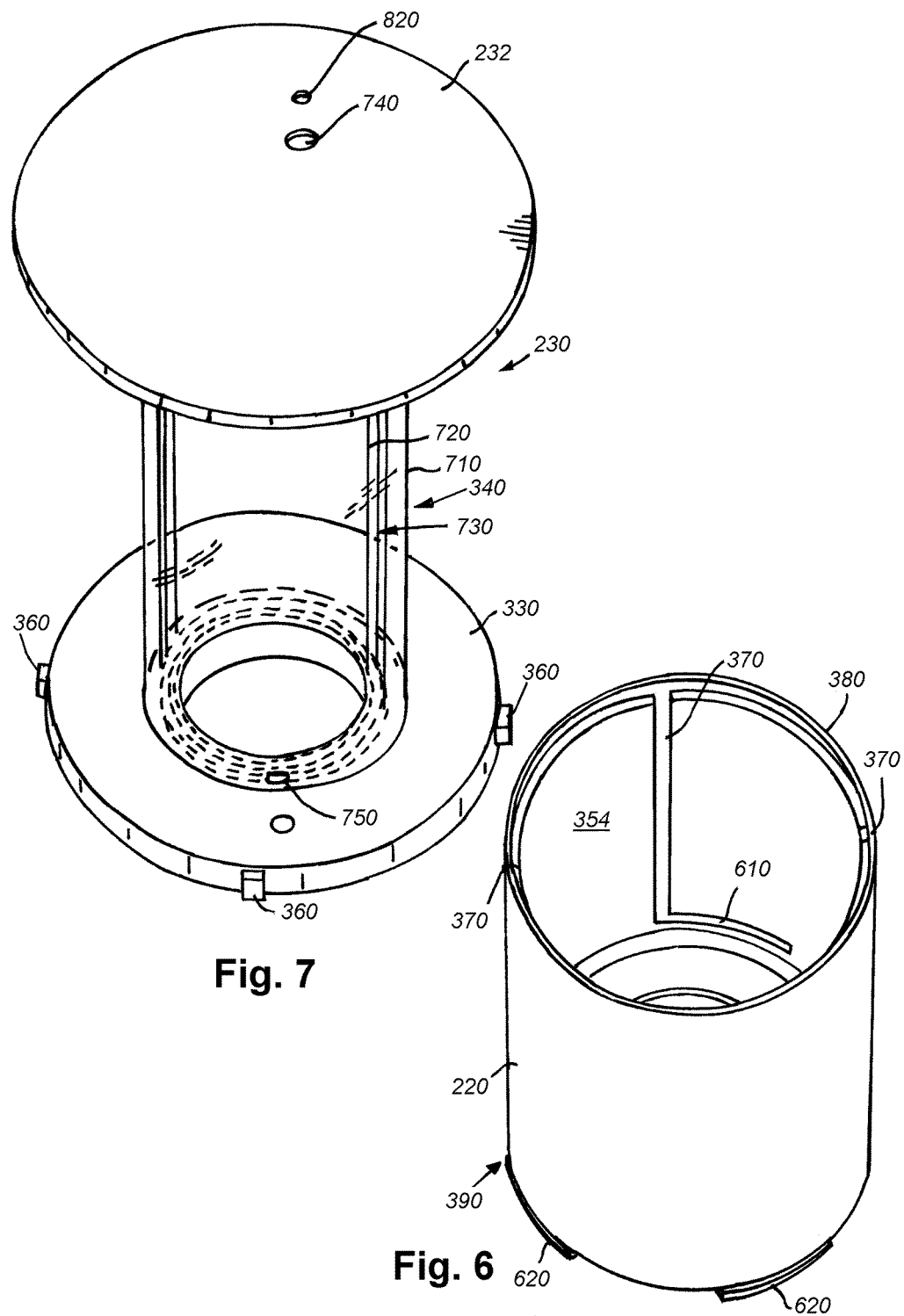
FIG. 6 is a perspective view of the canister of FIG. 2 detailing the cassette locking slots.
FIG. 7 is an exposed perspective view of the cassette of FIG. 2 showing the positioning of the inner and outer walls that define the fluid chamber and the outlet and inlet ports through each of the cassette's top cap and the bottom cap.

With further reference to FIGS. 5 and 6, the axial grooves 370 terminate in 90-degree-angled, L-shaped circumferential grooves 610. As such, when the cassette 230 is lowered into the canister, with the lugs 360 riding along the grooves 370, the cassette 230 can be eventually rotated about the common axis with respect to the canister 220, with the lugs 360 captured by the circumferential grooves 610. In this position, the cassette 230 is locked in place with the bottom surface of the top cap 232 engaged against the top rim 380 of the canister 220. This effectively prevents escape of any UV light that may inadvertently expose bystanders. The engaging rim of the top cap 220 can also include an elastomeric seal (not shown), such as an O-ring, to further prevent leakage of light from within the canister.

As further shown in FIGS. 5 and 6, the canister 220 is removable to assist it in serving the base unit 210. The bottom end 390 of the canister includes four circumferentially spaced lugs or cams 620. These lugs/cams 620 are sized and arranged to pass into cutouts 510 within a well structure 520 on the base unit that surrounds the lamp 310. The cutouts 510 divided by overlying shoulder sections 530. When the canister 220 is rotated, after seating in the well 520, the shoulders 530 then overlie the lugs 620 to axially secure the canister 220 within the base unit 210. As shown, the tubular lamp 310 extends from a lamp base 550 that engages a conforming two-pin lamp socket 560. In an illustrative embodiment, the lamp 310 comprises a 13-watt PL-S type lamp available from Phillips of the Netherlands. The lamp emits UV-C at a wavelength of approximately 254 nm. In general, it is desirable that UV-C in the range of approximately 100-290 nm be employed. Since the canister 220 is designed for reuse, the canister should be able to survive long-term exposure to such wavelengths (e.g. up to approximately 300 nm) without degradation. A tubular lamp 310 of this kind is advantageous in that the lamp base 550 is provided on only side, thereby allowing the socket 560 and all underlying electronics to remain within the base unit 210. This connectivity arrangement results in less structural interference to passing a cassette 230 over the lamp 310. A variety of electronics and power supply circuitry can be provided within the base unit 210. In general, this circuitry is enclosed by the base enclosure, and can be sealed against fluid infiltration for further safety. Such electronics typically includes a conventional fluorescent-lamp ballast (not shown) that provides the proper voltage and operating frequency for the lamp 310. The electronics for driving/controlling the lamp 310 can be conventional and known to those of ordinary skill. The base unit 210 can also include appropriate cooling vents and/or a fan unit where appropriate. The well 520 or another portion of the interconnection between the canister and the base unit can include a microswitch 570, or another type of contact mechanism. The microswitch 570 prevents the lamp 310 from operating without the canister 220 in place on the base unit 220. This further ensures that a bystander is not inadvertently exposed to UV light.

Reference is now made to FIG. 7, which shows the cassette 230 in further detail. The top cap 232 and the bottom cap 330 are shown, separated by the illustrative, cylindrical fluid chamber assembly 340. The fluid chamber assembly consists of an outer wall 710 and an inner wall 720. The top and bottom caps 232 and 330 act to secure and align (concentrically) the walls 710 and 720, using opposing cap rim structures (described below), so as to form therebetween a relatively thin-radius fluid chamber 730. In an embodiment, the fluid chamber 730 is no more than approximately 0.75-3.0 millimeters in thickness (radially). This allows the fluid chamber to draw fluid by capillary action from the lower inlet 750 through the chamber 730, to an upper outlet 740, where it is directed distally to the patient. As described above, this capillary action, along with the bottom-filling flow direction helps to de-air and de-bubble the chamber 730 without the need of external evacuation mechanisms. The thin fluid surface also assists in providing maximum UV exposure to the fluid volume by limiting the thickness through which the UV must pass, while enhancing the overall surface area of exposure of the fluid per-unit-time. The axial length and thickness of the chamber can be varied based upon the desired fluid flow rate. Generally, a larger, thicker chamber can be employed for higher fluid flow rates, while a smaller, thinner chamber can be employed for lower fluid flow rates.

The inner cassette wall 720 is constructed from a cylinder of a highly UV-transmissive material. In a reusable version of the cassette, quartz glass can provide an effective material due to its high UV transmissibility. Where the cassette is designed to be disposable, long-term damage to the chamber by UV is a significantly reduced concern—the cassette may be used for no more than approximately 12 hours in many implementations. Thus, a UV-transmissive polymer, such as fluoropolymer (for example commercially available Teflon® material) can be employed. The outer wall 710 can be constructed from a thicker, more-structural material, such as polycarbonate without regard to UV-transmission properties. Rather, the outer wall 710 can be illustratively filled with a UV-opaque or UV-reflective material to return UV light back to the fluid within the fluid chamber 730. The materials used throughout the construction of the cassette 230, canister 220 and base unit 210 are highly variable. Where materials are meant to survive long-term exposure to UV and the outer environment, they should illustratively be constructed from appropriately shielded or UV-resistant materials and/or provided with resistant coatings. Polycarbonate, or a similar material, can be used for most components. Generally, the caps and outer canister can be constructed from medical-grade (USP Class V minimum) plastic that is rated to block UV-C light in embodiments where the subcomponents are reusable. Where components are disposable, less UV-damage-resistant, medical-grade plastics can be employed. In general, in both disposable and reusable versions of the cassette, the top cap should be constructed from a material or provided with a coating that resists UV transmission for at least a specified time period. The base unit 210, more particularly, should be composed of a material (such as polycarbonate or sheet metal) exhibiting a high specific heat, or an efficient dissipation of heat, and that maintains rigid structural integrity after long-term UV exposure.

Figure 8:
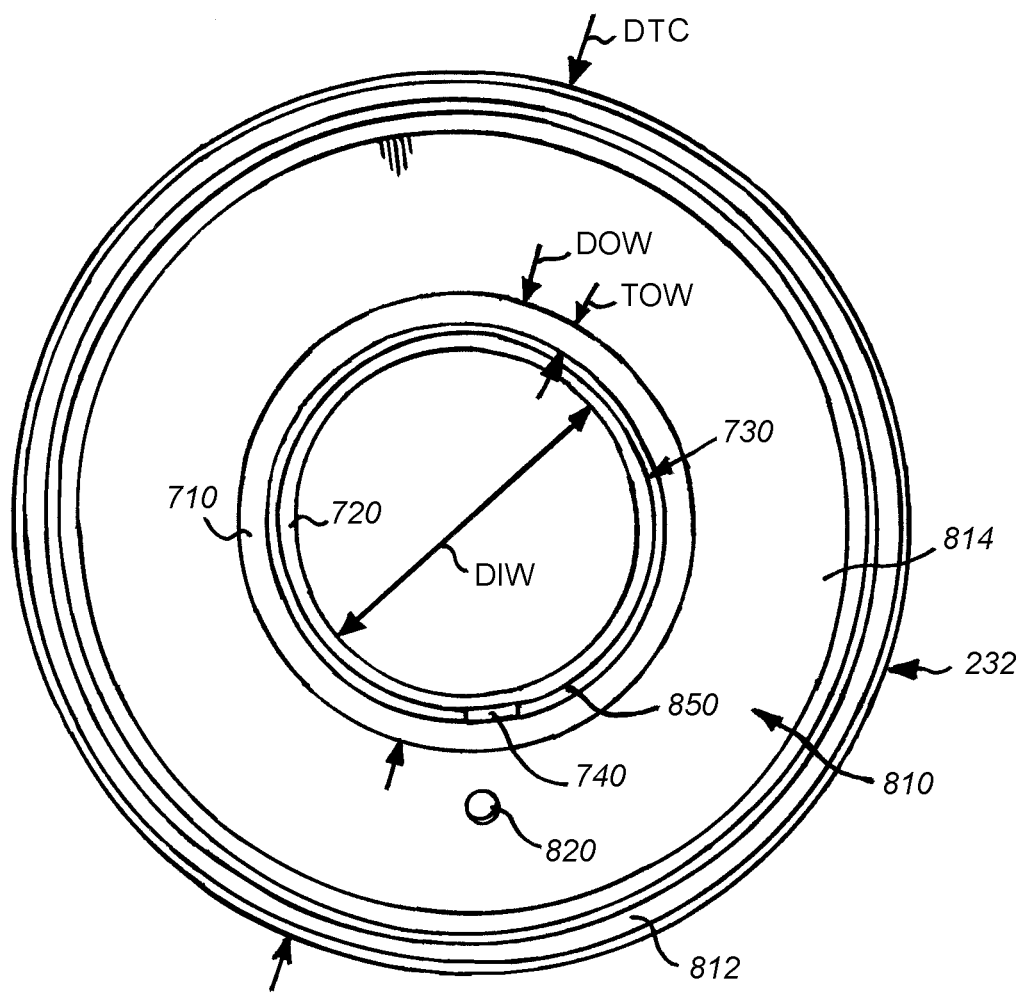
FIG. 8 is a bottom plan view of the cassette top cap of FIG. 7 detailing the concentric grooves and an intervening rim for receiving and spacing-apart each of the separated inner wall and the outer wall of the fluid chamber.

With reference to FIG. 8, the bottom surface 810 of the top cap 232 is now shown in further detail. The outer perimeter edge 812 of the cap 232 includes a recess that has been sized to engage the top edge 380 of the canister 220. It can include an elastomeric seal to ensure minimal leakage of UV-light therefrom when the cap 232 lockingly engages the canister after a twist-lock action is completed. Radially inward of the rim 812 is a flattened surface 814 that resides outside of the fluid chamber 730. The fluid chamber 730 is likewise defined by the outer wall 710 and inner wall 720 of the fluid chamber assembly 340. The outer wall 710 is illustratively radially thicker, as described below, to provide more structural integrity to the assembly. As noted above, the inner wall 720 is typically radially thinner to allow for better UV transmission from the lamp 310 into the fluid contained within the chamber 730. The inner diameter DIW of the inner wall is approximately 34 millimeters in an illustrative embodiment. In this manner, it will fit over the lamp 310 without interference, but still maintain a relatively close proximity to the lamp for effective UV transmission into the effluent chamber 730. All dimensions can be varied to accommodate differing sized lamps and/or flow rates, among other factors. In an illustrative embodiment, the outer wall 710 defines an outer diameter of DOW of approximately 44 millimeters and a radial thickness TOW of approximately 2.5 millimeters. The overall diameter DPC of the top cap 232 can be approximately 80-100 millimeters with the canister 220 defining a slightly smaller outer diameter. In this manner, the user's hand can discretely grasp the cassette rim 812, rotate it, and withdraw the cassette 230 axially from the canister 220 as desired. The planar space 814 allows for the placement of the inlet bridge tube (350) through-port 820 outside of both the lamp region and the fluid chamber assembly 340. The through-port 820 defines a diameter that is the same as or slightly larger than a conventional tubing. The inlet bridge tubing 350 thereby extends from the top side of the cassette 230, through the through-port 820, along the outer wall of the fluid chamber assembly 340, and thereafter through the bottom cap 330 to interconnect with the bottom inlet 750. The fluid thereafter flows upwardly through the chamber 730 to reach the outlet 740.

Figure 9:
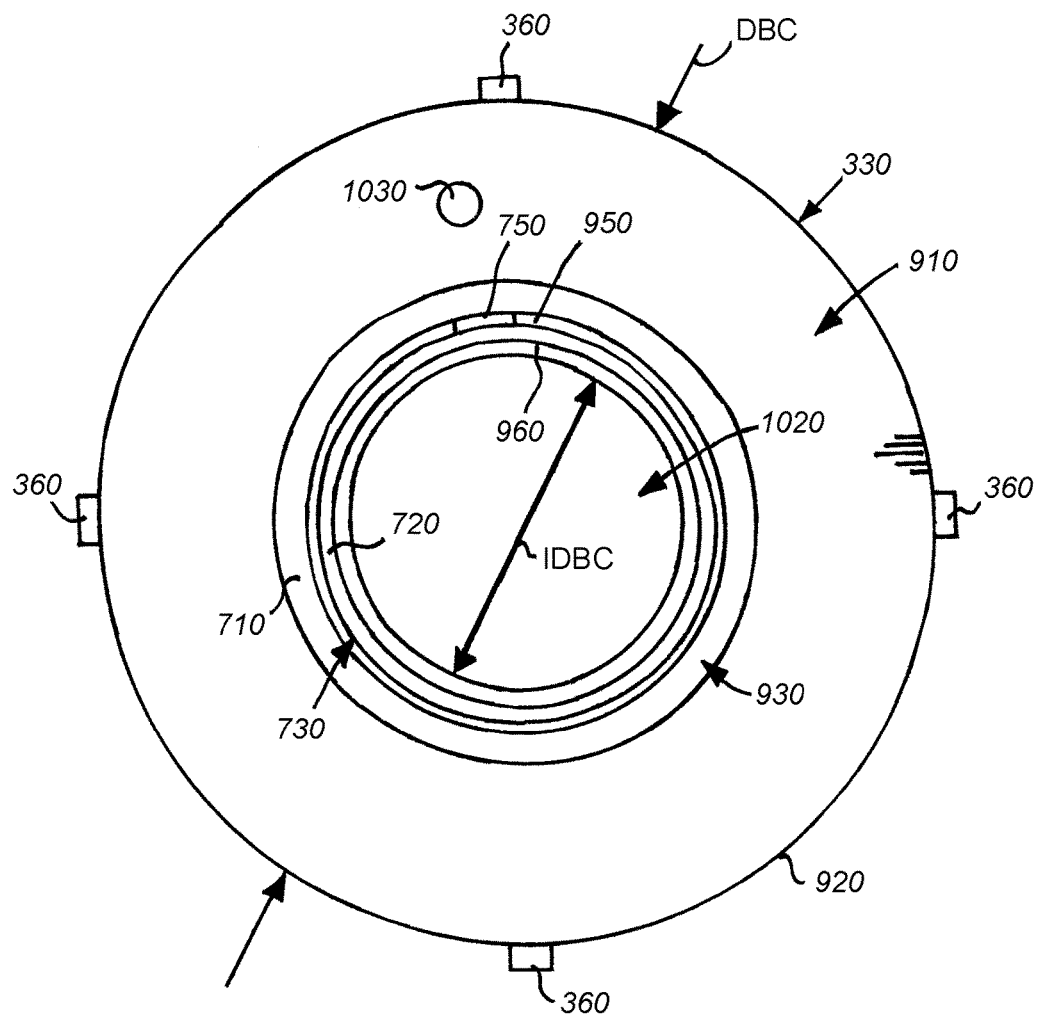
FIG. 9 is a top plan view of the cassette bottom cap of FIG. 7 detailing the concentric grooves and an intervening rim for receiving and spacing-apart each of the separated inner wall and the outer wall of the fluid chamber.

The outlet 740 defines a small through-hole located at a break in a rim 850 between the outer wall 710 and the inner wall 720. The rim 850 and adjacent wells maintain concentricity between the walls 710, 720. A similar rim structure is employed for the bottom cap 330 as shown in FIG. 9. The upper surface 910 of the bottom cap 330 defines an outer perimeter 920 having a diameter DBC that is the same as, or slightly smaller than, the inner diameter of the canister 220. As described above, the lugs 360 extend beyond the diameter DBC and are thereby arranged to nest within grooves 370 in the inner surface 354 of the canister 220. The close-conforming relationship of the lugs 360, grooves 370 and perimeter 920 (with respect to the canister inner diameter) ensure that the cassette 230 can be inserted concentrically into the canister without significant skew. In this manner, the cassette 230 avoids any contact between the inner wall 720 and the lamp 310, which might damage the lamp and/or inner wall. The overall concentric rim and well structure 930 of the top surface 910 of the bottom cap 330 provides recesses (wells) for receiving the inner wall 710 and outer wall 720 with a separating rim 950 therebetween. A further reinforcing rim 960 is provided radially inward of the inner wall 720. The inner diameter IDBC of the bottom cap 330 is open to allow the bottom cap to pass over the lamp 310, and thereby bring the lamp into confronting alignment with the fluid chamber 730. The inner diameter IDBC can be between approximately 25 and 30 millimeters in an illustrative embodiment. Other diameters can be defined to accommodate lamps/light sources of differing sizes. Likewise, the overall dimensions of the top/bottom caps and fluid chamber assembly therebetween can be varied to accommodate differing-sized lamp elements and arrangements. The rim 950 is broken in the region of the inlet hole 750. This allows fluid to pass through the cap 330 from the inlet bridge tube 350, and into the fluid chamber 730.

Figure 10:
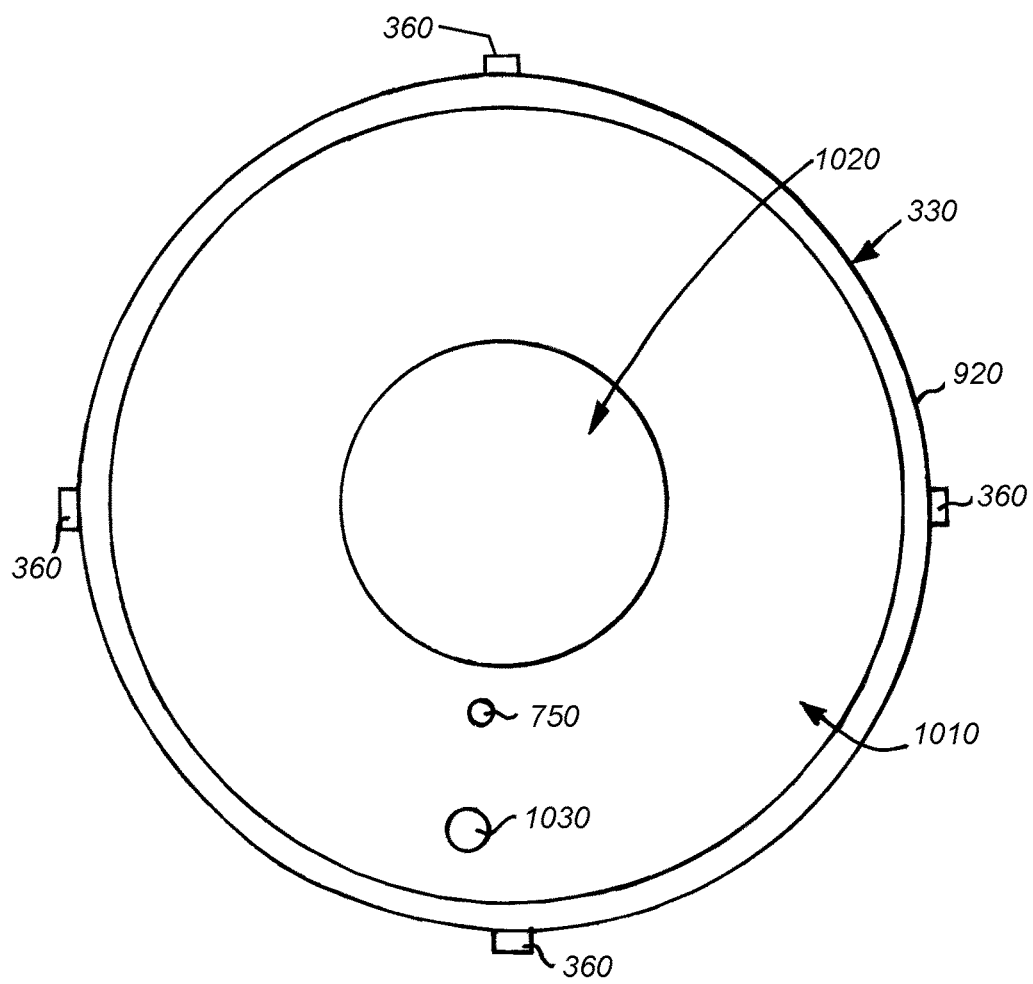
FIG. 10 is a bottom plan view of the cassette bottom cap of FIG. 7.
Figure 11:
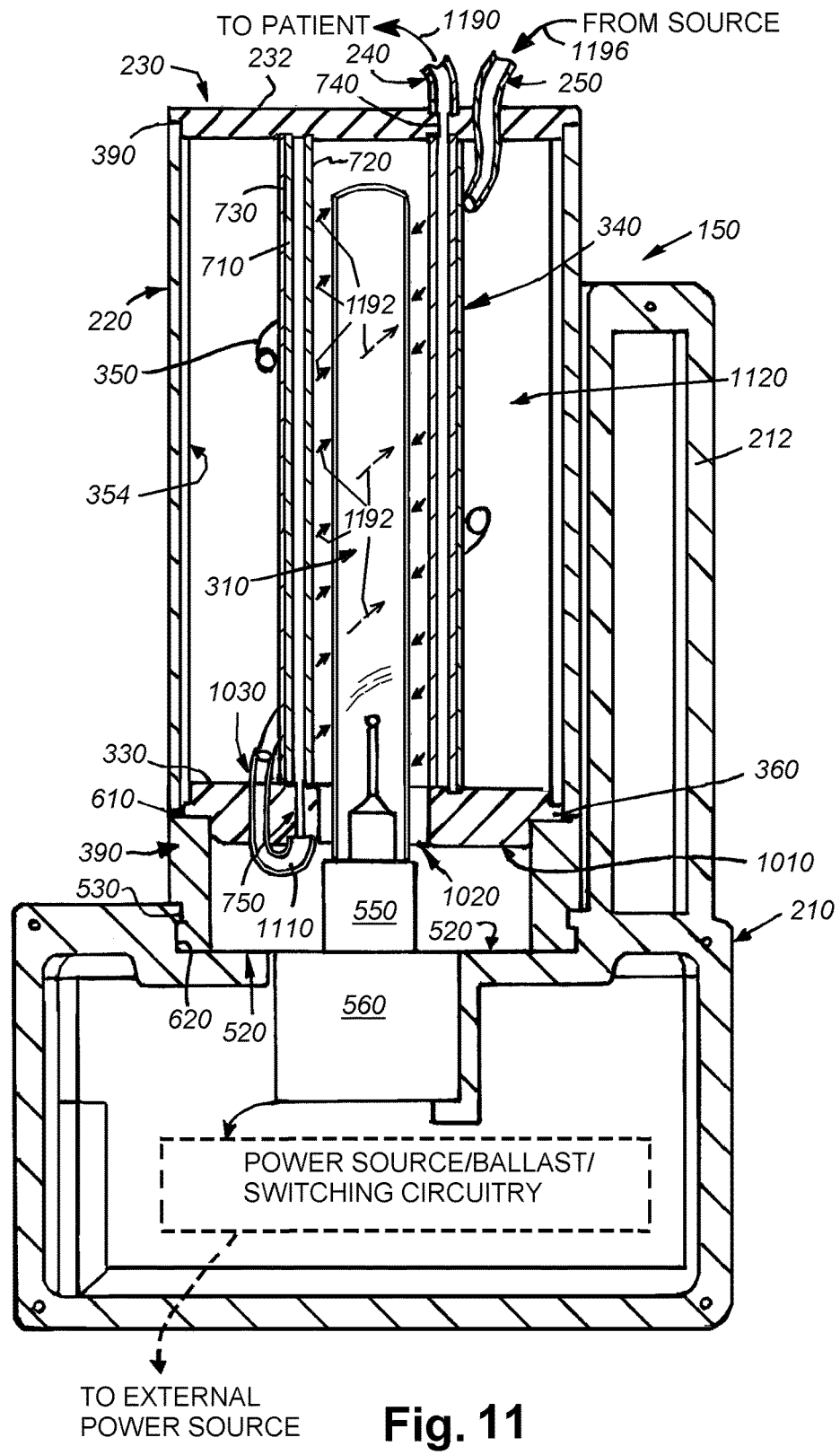
FIG. 11 is a side cross section of the assembled sterilization unit of FIG. 2.

The bottom side 1010 of the bottom cap 330 is shown in further detail in FIG. 10. The central orifice 1020 allows the bottom end of the cassette 230 to be passed over the lamp 310. As described above, the inlet hole 750 provides a mechanism for the bridge tube section 350 of the inlet tube 250 to interconnect with the through-port 1030. The through-port 1030, along with the top cap's through-port 820 provide a passageway for the bridge tube 350 to extend from the bottom inlet 750 back through the exposed top side of the top cap 232. This path is shown further in the cross sectional view of the sterilizer 150 in FIG. 11. As depicted, a 180-degree loop 1110 of the bridge tubing 350 exits the inlet hole 750 and passes back through the through-port 1030 in the bottom cap 330. The bridge tube 350 extends around the outer wall 710 of the fluid chamber assembly 340 of the cassette 230. The bridge tube 350 resides within the space 1120 formed between the outer wall 720 and the inner surface 354 of the canister 220. The lugs 360 and circumference of groove 610 are positioned so that the bottom surface 1010 of the bottom cap is spaced by approximately 1-2 centimeters above the well 520. In this manner, sufficient clearance for the loop 1110 of tubing is provided. This clearance also ensures that the lamp base 550 is located below the fluid chamber 340 so that part of the chamber 730 does not confront an unlit portion of the lamp 310.

Figure 11A:
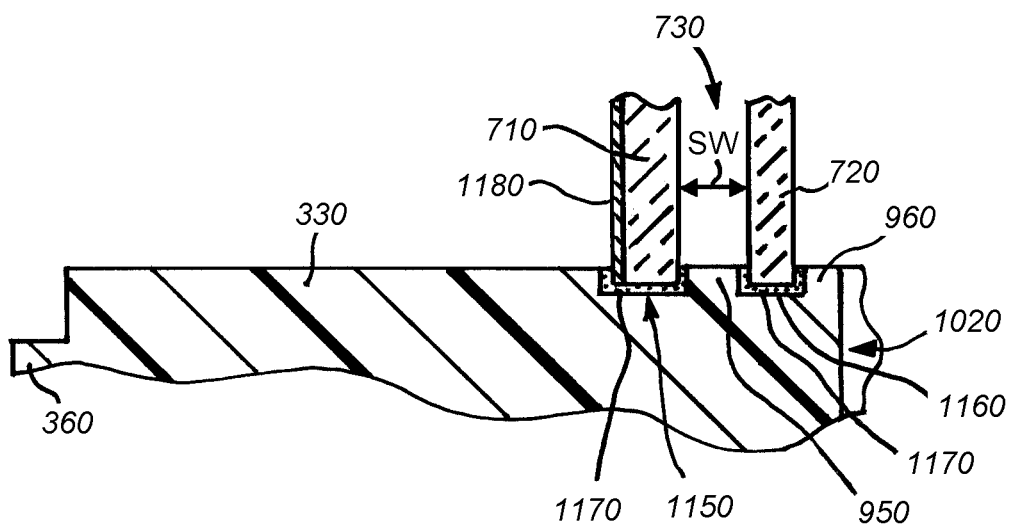
FIG. 11A is a more-detailed fragmentary cross section of the interconnection between the concentric slots of the bottom, cap of FIG. 7 and each of the inner wall and the outer wall of the fluid chamber.

With further reference to the fragmentary cross-section FIG. 11A of the interface between the walls 710, 720 and the bottom cap 330, each wall 710, 720 is seated within a respective groove 1150 and 1160, which are separated by the rim 950. Each wall 710 and 720 is sealed with respect to the groove 1150 and 1160 by medical-grade silicone sealant 1170 or another appropriate sealing compound/mechanism. The silicone also acts to maintain the structural integrity of the overall cassette assembly by resisting axial disconnection of the caps 232, 330 from the walls 710, 720. As noted, the outer wall 710 is generally more structural and thicker than the inner wall 720, which is adapted to provide improved UV transmission. The outer wall can be filled with a UV-reflective material or can include on an outer surface a UV-opaque and/or UV-reflective coating 1180. In alternate embodiments, no coating is provided, and all UV shielding is accomplished by the shielding of the canister, in combination with that of the top cap 232.

Figure 12:
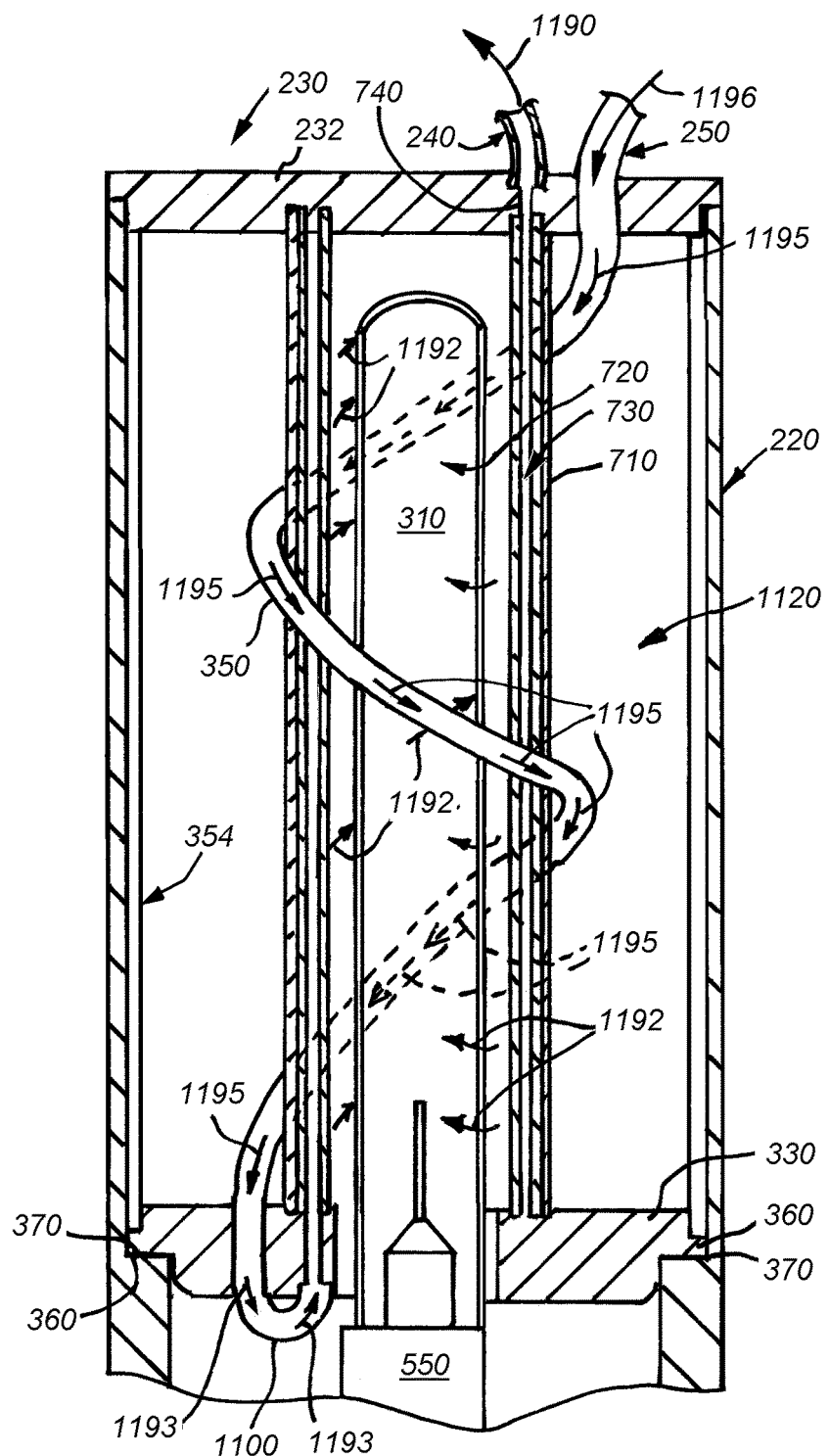
FIG. 12 is a partial side cross section of the sterilization unit of FIG. 2 detailing an exemplary fluid flow therethrough.

With reference also to FIG. 12, the generalized flow of fluid through the cassette 230 is depicted. Fluid enters the inlet 250 (arrow 1196) and passes downwardly through the bridge tube section 350 (arrows 1195), within the space 1120 between the exterior of the fluid chamber assembly 340 and within the wall of the canister 220. It then passes through the bottom cap and around (arrows 1193) a 180-degree-turn loop 1110 of the tube 350. The fluid enters the inlet hole 750 and travels upwardly travels around the fluid chamber (arrows 1192) until it enters the outlet hole 740 within the top cap 232. The fluid eventually exists through the outlet 240 (arrow 1190) to travel down a breach-free distal section of the distal tubing (134) to the patient or other destination requiring a sterile fluid. Note that the flow pattern through the cassette 230 and fluid chamber 730 described herein is only exemplary of a variety of pathways that fluid can travel through the cassette 230. In an alternate embodiment, fluid can enter through the top and exit through the bottom of the cassette. Likewise, the concentric walls of the cassette can define passageways that actively route fluid both downwardly and upwardly so that inlets and outlets from the chamber can be located on one side of the cassette without employing a return tube. Likewise the upward return of fluid can be accomplished by an internal conduit defined by walls within the fluid chamber or another integral conduit structure associated therewith and attached to the fluid chamber assembly. Alternate mechanisms for allowing entry of fluid into the fluid chamber, such as side ports, can also be provided. In further embodiments, fluid can travel at a horizontal or otherwise non-orthogonal direction with respect to gravity. Additionally, while a small-diameter inlet and outlet hole 750, 740 is shown interfacing with a larger diameter tubing at a step, the geometry of the hole can be highly variable—providing a variety of smooth transitions, tapers and the like to facilitate a lower-resistance fluid flow.

Figure 13:
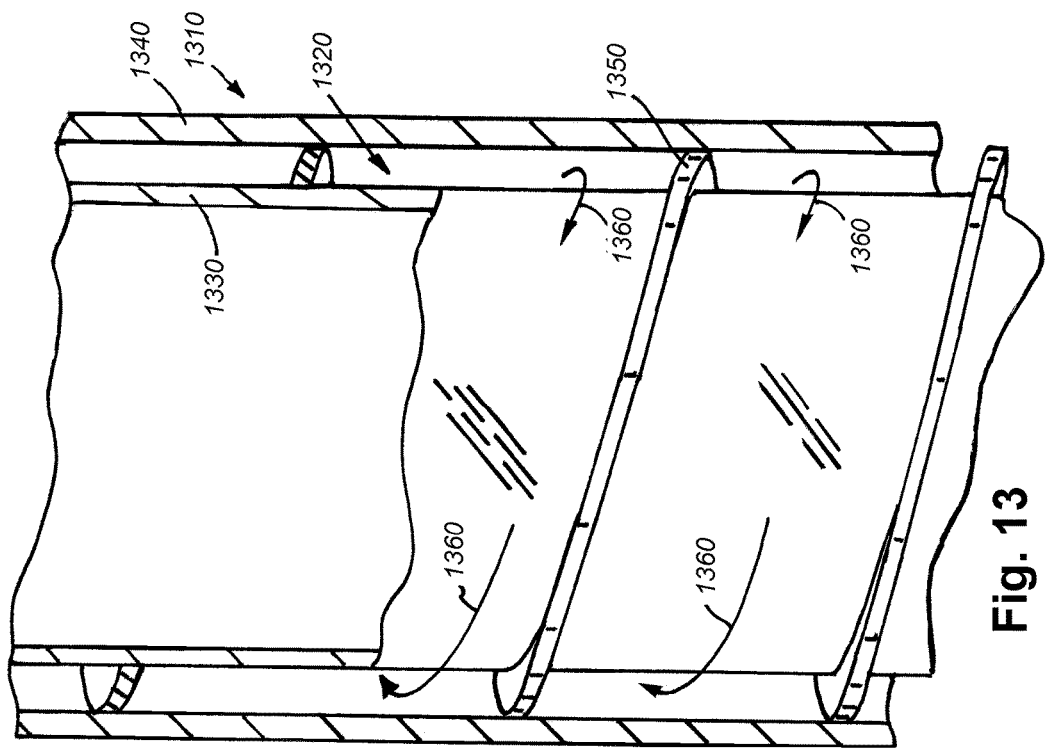
FIG. 13 is a partial cross section of a cassette inner wall, outer wall and fluid-guiding baffle arrangement therebetween according to an alternate embodiment.

In one alternate embodiment, shown in FIG. 13, the cassette fluid chamber assembly 1310 is provided with a fluid chamber 1320 having a pair of inner and outer walls 1330 and 1340 separated by a spiral baffle 1350. Thus, when fluid enters through the top cap, it travels around the spiral pathway (exemplary upward arrows 1360) until it exits the outlet in the bottom cap. This structure ensures that fluid travels a predetermined exposure path during which UV can act upon microorganisms within the fluid. A variety of other baffle arrangements can be provided in alternate embodiments, including those that direct fluid into and out of the same side of the cassette.

Figure 14:
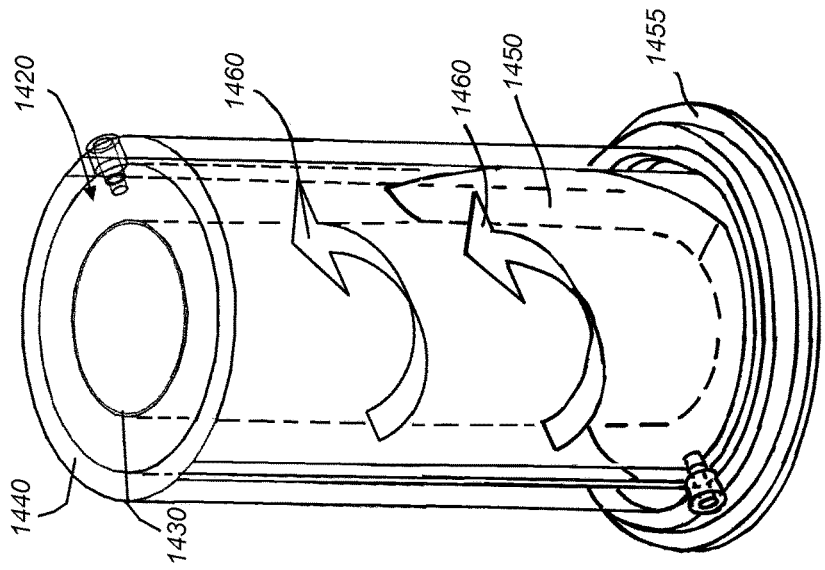
FIG. 14 is a perspective view of a cassette inner wall, outer wall and fluid-guiding ramp baffle arrangement according to a further embodiment.
Figure 15:
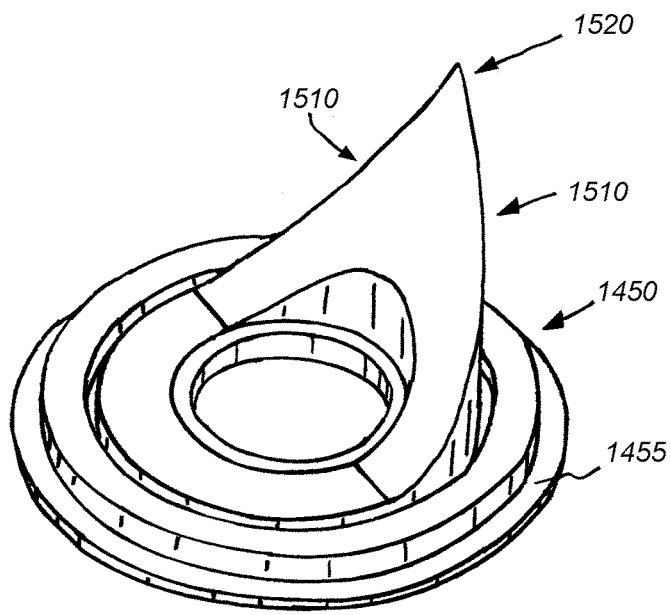
FIG. 15 is a perspective view of the bottom cap and fluid-guiding ramp baffle arrangement according to the embodiment of FIG. 14.
Figure 16:
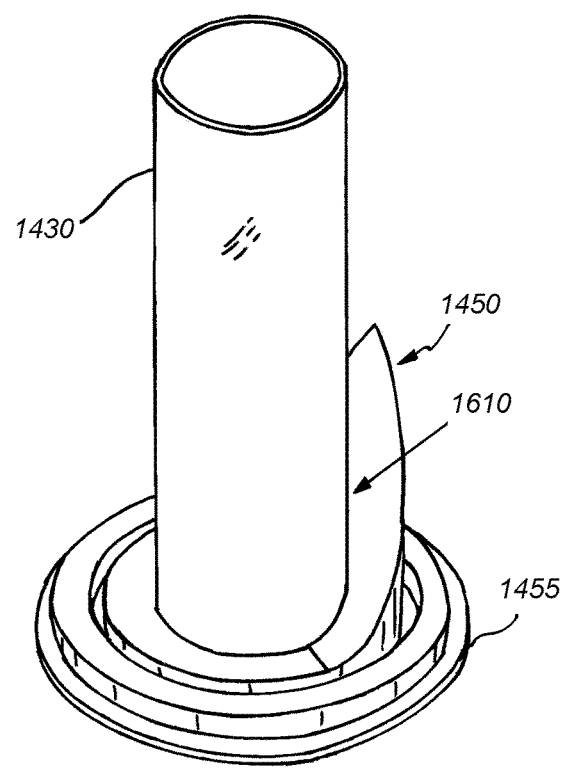
FIG. 16 is a perspective view of the cassette inner wall and ramp baffle arrangement according to the embodiment of FIG. 14.

In a further embodiment, shown in FIGS. 14-16, the cassette fluid chamber assembly 1410 is provided with a fluid chamber 1420 having a pair of inner and outer walls 1430 and 1440, respectively, separated by a ramp baffle 1450 on the bottom cap 1455. The ramp baffle 1450 is constructed and arranged to promote the spiraling flow of fluid within the fluid chamber 1420 to have an even, prolongated and more direct contact with the light (UV) source, disposed within the inner wall 1430, as fluid travels in a spiral pathway (arrows 1460). The spiral pathway allows for a larth surface area and small fluid depth for the maximum exposure to the UV light source.

As shown in greater detail in FIG. 15, the ramp baffle 1450 includes a pair of ramping portions 1510 which are joined at a joint 1520 such that fluid is directed in a spiraling flow to improve and prolong UV radiation, and thereby sterilization. As shown in FIG. 16, the ramp baffle 1450 is a single solid member that contacts the inner wall 1430 at point 1610. This embodiment provides a single thick walled baffle 1450 for directing and promoting spiral fluid transfer and exchange.

Note, while the illustrative embodiment shows tubings mounted directly to the top and bottom caps, using, for example, adhesive, welding or other joining techniques, it is expressly contemplated that other mechanisms for securing inlet, outlet and return tubing to the cassette can be employed. For example, the inlets and outlets can be provided with molded-on or affixed Luer fittings. Likewise, while the fluid chamber is served by smaller-diameter inlet and outlet holes/ports, these structures can taper outwardly toward respective interconnected tubings/conduits to provide a more-gradual transition between the larger-diameter fluid conduit and the smaller-diameter interface with then fluid chamber. In addition, the interface into the fluid chamber and that inlet or outlet can maintain a similar overall orifice area by elongating the entry port along the direction of the separating rim between walls. That is, the inlet and outlet can define an arcuate slot within the rim that defines an area equivalent to the circular conduit defining the attached inlet or outlet.

It should be clear that the above-described sterilizer advantageously eliminates microbiological contaminants from a fluid flow without compromising the flow rate or suffering from eventual flow degradation due to clogging. It uses relatively little energy and no harsh or potentially toxic chemicals. It is also less likely to generate resistant strains of microorganisms over time. It is superior to prior systems generally employing pulsed UV radiation to inactivate microorganisms—for example, systems employing broad-spectrum, polychromatic light pulses, including somewhat complex assemblies that incorporate reflective surfaces. It is noted that one device of this kind has been described which allows for the adjustment of radiation wavelengths to any range within 120-2600 nm. However, such a device disadvantageously is designed to sterilize a stationary package, rather than a flowing fluid system as contemplated by the novel embodiments herein. Likewise, the above-described system advantageously avoids disadvantages of other prior art, such as those that describe techniques for sterilization of medical devices and their packaging, including the fluid in which the device is suspended, using wavelengths of radiation and intensities including or entirely within the UV range—as none deal with flowing fluid systems. Moreover, unlike a particular prior art system, which provides for UV sterilization of an intravenous catheter lumen for an ex vivo purpose (disinfection of a device and not the fluid destined to course through the device) the novel system described herein provides for sterilization of the internal fluid.

The foregoing has been a detailed description of illustrative embodiments of the invention. Various modifications and additions can be made without departing from the spirit and scope of this invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. For example, perimeter shape of various walls in the fluid chamber and canister can be non-circular. For example, the walls could be polygonal, oval or an irregular shape. It is desired mainly that a large surface area of flowing fluid at a predetermined rate be exposed for a sufficient time to a given intensity of microorganism-killing UV radiation to render the fluid effectively sterile. This arrangement is constructed to effectively maximize the area of exposure of the fluid to the UV radiation while accommodating a desired flow rate through the fluid chamber. While it is contemplated that some fluids can be degraded by UV radiation, the illustrative embodiments herein provide effective non-damaging sterilization for a wide range of common IV fluids, and with appropriate care, the illustrative sterilizer can be employed in a wide range of therapeutic scenarios. In alternate embodiments, some or all of the electrical components of the system can be remote—for example residing in a control box near a wall outlet. Fiber-optic material/conduits can be thereby used to convey the UV radiation, i.e. an external fiber-optic cable can convey the light from a remote source. Also, while a particular set-up procedure for the sterilizer assembly have been described herein, this procedure can be further varied or augmented as needed to satisfy the needs of the treatment protocol, practitioner, or patient. For example, the distal outlet and tubing of the sterilizer can be connected to another device or set of devices, rather than a parenteral access point (patient) that require a sterilized flow of fluid. Accordingly, this description is meant to be taken only by way of example, and not to otherwise limit the scope of this invention.

What is claimed is:

1. A method for rendering parenteral infusion fluid sterile, distal to potential breaches in sterile integrity comprising the steps of:
 providing a source of infusion fluid;
 sterilizing the infusion fluid at a fluid chamber that interacts with a UV source so as to receive the fluid as the fluid flows by capillary action at a predetermined rate through the fluid chamber and subject the fluid to radiation from the UV source; and
 directing sterilized fluid from the fluid chamber to a parenteral location along a conduit distal of points requiring breach points.

2. The method as set forth in claim 1 wherein the step of sterilizing includes providing a disposable cassette to a housing containing the UV source.

3. The method as set forth in claim 2 wherein the step of providing includes removably engaging the disposable cassette in a housing that contains a canister that shields the UV source from external transmission of UV radiation.

4. The method as set forth in claim 3 wherein the step of removably engaging includes twistably locking each of a top end cap and a bottom end cap of the cassette into the canister with the UV light source passing through a central space that confronts a UV-transmissive inner wall of the fluid chamber.

5. The method as set forth in claim 1 where the step of receiving the infusion fluid includes directing the fluid approximately upwardly, with respect to a direction of gravity, from a bottom inlet in the fluid chamber to a top outlet in the fluid chamber.

\* \* \* \* \*